US010067105B2

(12) United States Patent
Deilmann et al.

(10) Patent No.: US 10,067,105 B2
(45) Date of Patent: Sep. 4, 2018

(54) METHOD FOR OPERATING A MEASURING SITE

(71) Applicant: KROHNE Messtechnik GmbH, Duisburg (DE)

(72) Inventors: Michael Deilmann, Essen (DE); Christoph Schmits, Dortmund (DE)

(73) Assignee: KROHNE Messtechnik GmbH, Duisburg (DE)

( * ) Notice: Subject to any disclaimer, the term of this patent is extended or adjusted under 35 U.S.C. 154(b) by 0 days.

(21) Appl. No.: 14/719,681

(22) Filed: May 22, 2015

(65) Prior Publication Data

US 2016/0018372 A1 Jan. 21, 2016

(30) Foreign Application Priority Data

May 23, 2014 (DE) .................. 10 2014 107 275

(51) Int. Cl.
*G01N 33/00* (2006.01)
*G01D 18/00* (2006.01)

(52) U.S. Cl.
CPC ....... *G01N 33/0006* (2013.01); *G01D 18/008* (2013.01); *G01N 33/0036* (2013.01)

(58) Field of Classification Search
CPC ........... G01N 33/0006; G01N 33/0036; G01D 18/008
USPC ......................................... 73/1.06
See application file for complete search history.

(56) References Cited

U.S. PATENT DOCUMENTS

| 6,510,397 | B1* | 1/2003 | Choe ................... F16H 57/0006 |
| | | | 702/104 |
| 7,957,928 | B2 | 6/2011 | Tischendorf et al. |
| 8,005,629 | B2 | 8/2011 | Steinmueller et al. |
| 8,463,559 | B2 | 6/2013 | Lohmann et al. |
| 9,164,057 | B2 | 10/2015 | Pechstein et al. |
| 2006/0155511 | A1* | 7/2006 | Steinmueller ............ G01D 3/08 |
| | | | 702/176 |
| 2009/0132194 | A1* | 5/2009 | Tischendorf ....... G01N 27/4163 |
| | | | 702/104 |

(Continued)

FOREIGN PATENT DOCUMENTS

| DE | 102007039265 A1 * | 2/2009 | ............ G01D 3/022 |
| DE | 10 2010 062 657 A1 | 6/2012 | |

(Continued)

OTHER PUBLICATIONS

Translation DE 102010062657 A1.*
Translation DE102007039265.*

*Primary Examiner* — Natalie Huls
*Assistant Examiner* — Monica S Young
(74) *Attorney, Agent, or Firm* — David S. Safran

(57) ABSTRACT

A method for operating a measuring site (1), wherein a measured variable is determined by a sensor (5) that can be calibrated and in which an exact as possible planning of activities, to which, for example, calibration or sensor replacement belong, is possible is obtained, in accordance with the method, in that the sensor (5) is calibrated at presettable calibration points in time, that at least one parameter in conjunction with calibration is stored as a part of reference data of the sensor (5) and that at least one aging-dependent variable of a sensor (8, 6) differing from the sensor (5) is estimated based on reference data of the sensor (5).

7 Claims, 3 Drawing Sheets

(56) References Cited

U.S. PATENT DOCUMENTS

2012/0144894 A1* 6/2012 Trapp ............... G01N 35/00693
                                                     73/1.06
2014/0278186 A1* 9/2014 Herzl ................. G01N 33/0006
                                                     702/104
2014/0347033 A1* 11/2014 Dymek .............. G01R 19/0092
                                                     324/76.11

FOREIGN PATENT DOCUMENTS

DE      102010062657 A1 *  6/2012   ........... G01D 18/008
WO       2004/025223 A2     3/2004

* cited by examiner

METHOD FOR OPERATING A MEASURING SITE

BACKGROUND OF THE INVENTION

Field of the Invention

The invention relates to a method for operating a measuring site, wherein at least one measured variable is determined at the measuring site by at least one sensor that can be calibrated. Furthermore, the invention relates to a method for operating a second measuring site, wherein at least one measured variable is determined by at least one, second sensor at the second measuring site.

Description of Related Art

In the field of analytical measuring, the measuring sensors used are partly regularly replaced, since they are subject to natural aging. Additionally, particular situations can arise that make a replacement necessary. For example, a buffer solution having a pH of 7 can contaminate a pH sensor or the electrode of the probe shows an incorrect measured value. Such sensors and other sensors are generally calibrated at regular intervals.

In order to estimate the lifespan of a sensor, it is known from the prior art to use state parameters or test parameters to extrapolate future behavior (see, e.g., International Patent Application Publication WO 2004/025223 A2 and corresponding U.S. Pat. No. 8,005,629).

This relates to a measuring site, at which a sensor determines at least one measured variable. The operation of such a measuring site is related to the carrying out and planning of calibrations or the timely replacement of used sensors. The latter makes knowledge about the remaining life of a sensor necessary.

SUMMARY OF THE INVENTION

Thus, the object of the invention is to provide a method for operating a measuring site of a processing system, in which, as an alternative to the prior art, an exact as possible planning of activities, to which, for example, calibration or sensor replacement belong, is possible.

The method according to the invention for operating a measuring site, wherein at least one measured variable is determined at the measuring site by at least one sensor that can be calibrated and in which the above derived and described object is met, is initially and essentially characterized in that the sensor is calibrated at presettable calibration points in time, that at least one parameter in conjunction with calibration is stored as a part of reference data of the sensor and that at least one aging-dependent variable of a sensor differing from the sensor is estimated based on reference data of the sensor.

It is provided in one implementation, that the sensor is calibrated until the sensor malfunctions. In this implementation, reference data about an entire life cycle of a sensor at the measuring site is generated or obtained.

In an alternative or additional implementation, the sensor is calibrated until data in conjunction with calibration lie outside of a given tolerance band. If, for example, it is determined during calibration that the parameter lies outside of a tolerance band, or that the accuracy to be achieved lies outside of a tolerance band despite calibration, or that the duration for calibration is already outside of a tolerance band, then the series of calibrations with this sensor is stopped. This relates, thus, to the case that the sensor is still operable, but that it, due to signs of aging, no longer meets requirements that are defined or implemented by at least one tolerance band.

One implementation comprises a point in time—in particular for calibrating or for reaching a state of replacement—being estimated as aging-depending variable.

In an associated implementation, only one such point in time is estimated for the sensor differing from the sensor, the point in time lying temporally within a period of time spanning the points of time of calibration of the sensor.

For the estimation, in particular, only one interpolation is carried out using the stored reference data and the period of time associated with it. Carrying out an extrapolation at points in time for which no reference data is provided is particularly to be avoided.

If, for example, the reference data includes a lifespan of x months of the sensor, then only such points in time are estimated for another sensor that reach up to a lifespan of the other sensor of x months.

If, for example, reference data is obtained that lies between the start-up of the sensor as a zero point and a point in time T and that, thus, describes a lifespan of a sensor of T time units, then only points in time are estimated for another sensor that lie within these T time units.

In other words, if the reference data of the sensor relates to a duration of time that is less than the duration that the sensor differing from the sensor is operated, then no more estimations are made for the latter sensor, since the—e.g., only using an extrapolation—calculable points in time lie outside the time frame of the reference data.

The estimation of the points in time is, thus, based on measured or stored extrapolations and not on extrapolations obtained using different mathematical models.

In one design, interpolations are permitted, insofar as continual time lines or curves are generated from the individual calibration points in time using mathematical models.

It is provided in one implementation that the sensor is replaced by a replacement sensor at the measuring site.

In an associated implementation, the replacement sensor is calibrated at the presettable calibration points in time and that at least one parameter in conjunction with calibration is combined with the reference data of the sensor into sensor-type reference data of the measuring site. Thus, further reference data is obtained by the replacement sensor and combined with the reference data of the sensor into sensor-type reference data for the measuring site.

It is provided in an additional or alternative implementation that at least one measured variable is determined at a second measuring site by at least one second sensor and that at least one aging-dependent variable of the second sensor is estimated based on the reference data of the sensor. In this implementation, the method is used overall for operating the two measuring sites.

The measuring site and the second measuring site are located, in particular, at different sites of a processing system.

Thereby, in one embodiment the same or nearly the same process conditions prevail at the measuring site and the second measuring site (e.g., temperature, pressure, humidity, etc.).

In an alternative implementation, the reference data or the sensor-type reference data is converted or accordingly scaled in respect to the process conditions from the measuring site to the second measuring site.

Furthermore, the invention relates to a method for operating a second measuring site, wherein at least one measured variable is determined by at least one second sensor at the second measuring site. It is thereby provided that at least one aging-dependent variable of the second sensor is estimated based on reference data of a sensor determining at least one measured variable of a measuring site differing from the second measuring site.

The above statements and implementations thereby relate accordingly also to obtaining reference data or, optionally, sensor-type reference data, which is also based on the reference data.

When operating the second measuring site, the advantage arises here that already-present reference data from another measuring site can be used. Here, for example, a second measuring site can be created and, already, anticipated operation of the just-installed second sensor is possible due to the data obtained at the measuring site.

It is provided in one implementation that the pH value, the oxygen content, the chlorine content, the conductivity, the ozone content, the hydrogen peroxide content, the content of free chlorine, the content of residual chlorine, the turbidity, and/or the solids content is determined as measured variable with the sensor. In particular, the replacement sensor and/or the second sensor are designed according to the type of sensor.

The invention is thus described again in other words:

If, to the greatest possible extent, constant conditions typical for the process prevail at the respective measuring sites in processing systems, the measuring sensors at the respective measuring sites age over their lifespan due to similarly occurring effects of aging.

For this reason, a typical or characteristic course of aging is recorded by the sensor at the measuring site. This occurs by registering the parameters of the calibrations. These parameters change over the lifespan.

In one implementation, the reference data is used, for example, for estimating the lifespan of further sensors at the measuring site or at the second measuring site.

If the parameters of the calibrations are also recorded—preferably at the same measuring site—for subsequent replacement sensors, then this can be combined with the existing reference data, e.g., is averaged, in order to improve the accuracy of prediction.

In a further step, this model can be scaled so that the reference data of the measuring site is used at a second measuring site with other process conditions or is scaled for the differences in the process conditions.

Depending on the design of the sensor, storing reference data, estimating or adapting reference data into sensor-type reference data occurs in so-called transmitters or measuring transducers, in a control room, or in external devices.

In detail there is a number of possibilities for designing and further developing the method according to the invention as will become apparent from the following description of embodiments in conjunction with the accompanying drawings.

DETAILED DESCRIPTION OF THE INVENTION

Figure 1:
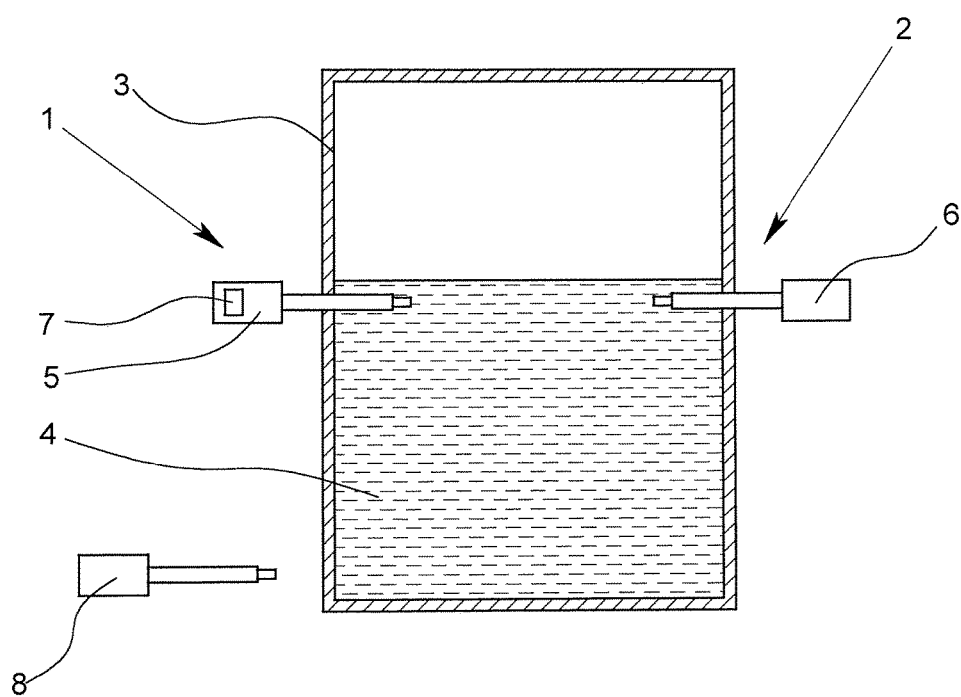
FIG. 1 is a cross-section view taken through a schematic representation of a part of a processing system.

In FIG. 1, a part of a processing system is schematically shown with a first measuring site 1 and a second measuring site 2. Both measuring sites 1, 2 differ in view of their position in the container 3, in which a medium 4 is located—a liquid, here.

In order to determine the pH value of the medium 4, a sensor 5 is installed at the measuring site 1 and a second sensor 6 is installed at the second measuring site 2. Both sensors 5, 6 are, in particular, of the same sensor type.

Sensor 5 is calibrated at different calibration points of time and the parameters associated therewith are stored as reference data in a storage unit 7. The parameters relate, for example, to the value that was converted from the measuring electrical voltage into the present pH value. A measure for the lifespan or for the age of the sensor 5 results from the parameter values.

The reference data of sensor 5 obtained from the performed calibration is used for estimating relevant points of time of the second sensor 6 at the second measuring site 2.

The use of reference data occurs here on the condition that essentially the same or comparable or periodic comparable or same process conditions are present at the measuring site 1 and the second measuring site 2. In an alternative design, adaptation of the reference data in view of different process conditions occurs.

If the sensor is no longer operational, it is replaced by a replacement sensor 8, which is of the same sensor type as sensor 5. Reference data from the previously installed sensor 5 is used for consideration of aging of the replacement sensor 8.

Figure 2:
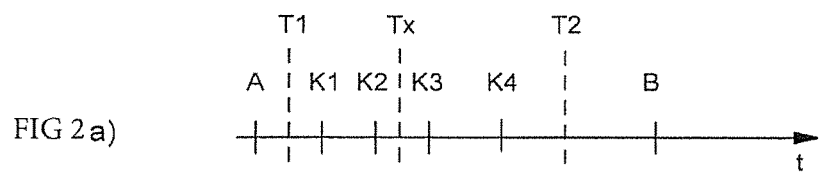
FIGS. 2*a* & 2*b* are two timelines with different points in time.
Figure 2:
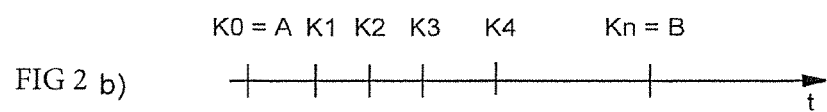

In FIGS. 2*a* and 2*b*, it is schematically explained using two time axes for time t how the calibration point in time and the point in time as estimated variable are associated according to one embodiment.

The sensor in FIG. 1 attached at the measuring site is put into operation at time A and is removed at time B as a result of malfunction. The malfunction can thereby relate to a complete termination of the measuring ability or also a measuring uncertainty due to aging effects beyond a given limit.

On the time axis of FIG. 2*a*, the sensor is calibrated at the points in time K1 to K4 and the parameters associated therewith are stored as reference data of the sensor in respect to the measuring site.

In the case of the time axis of FIG. 2*b*, the sensor is calibrated at two further points in time K0 and Kn. On the one hand, this is the point in time of start-up of the sensor, which is why K0 and A coincide. On the other hand, the calibration point in time Kn is when it is detected that the sensor is to be replaced. Thus, the points in time Kn and B coincide.

In the case of FIG. 2*a*—based on the reference data, for example, for the replacement sensor, which is located at the same measuring site, if a point in time Tx is estimated when calibration is necessary, then it is provided that this is related only to one point in time between K1 and K4 relative to time A or between A and B.

If, thus, for example, the replacement sensor is first installed at such a short time T1 between time A—as its zero point of installation and start-up—and K1, then the earliest estimated point in time for a calibration of the replacement sensor can be after time K1—thus, e.g., Tx.

Then again, there are also no points in time that can be estimated for a calibration that lie between the points in time K4 and B, which would be later than the space of time of the reference data. If, thus, the replacement sensor is in operation longer than the duration between A and K4—e.g., up to time T2,—then no point in time can be estimated, since these would be based on an extrapolation.

In contrast, the calibration points in time of FIG. 2b allow for a complete estimation range between installation (time A) and de-installation (time B) of the sensor.

Figure 3:
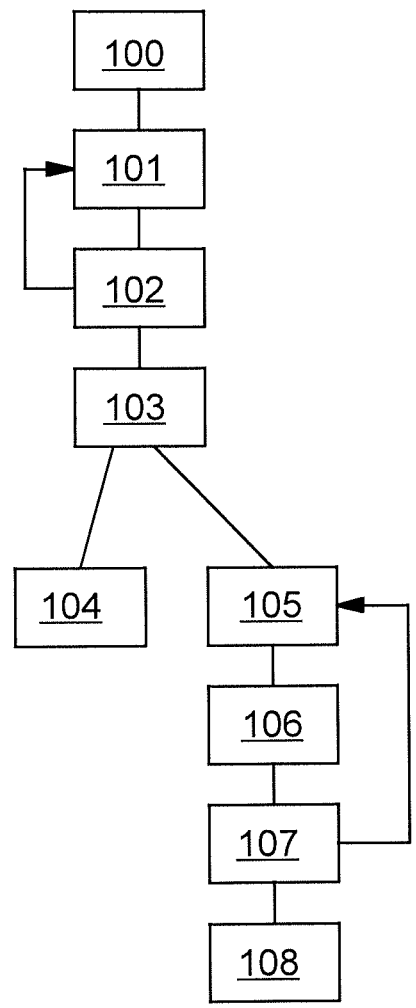
FIG. 3 is a flow chart of a method for operating a measuring site and a second measuring site.

A sequence for operation of the measuring site and the second measuring site of FIG. 1 can be taken from FIG. 3.

In step 100, the sensor is put into operation at the measuring site. The sensor is calibrated in step 101 and the parameters associated therewith—or at least one parameter associated therewith—are stored in step 102. Further calibrations 101 follow until the sensor is removed from the measuring site and replaced by a replacement sensor in step 103.

The replacement sensor is operated with reference data of the sensor in step 104, so that points in time for calibration or for exchanging the replacement sensor are estimated.

The replacement sensor is subjected to a calibration in alternative step 106, wherein the parameters associated therewith are stored in step 106 and the reference data of the sensor is processed with the data of the replacement sensor into sensor-type reference data of the measuring site in step 107. The parameter is averaged, for example, in the case of same calibration points in time—in respect to operation time.

The sensor-type reference data of the sensor type, to which the sensor and the replacement sensor belong, is thus overall more exact or has more calibration points in time than the initially obtained reference data.

This is also repeated for a given duration or, also, until the replacement sensor malfunctions.

The sensor-type reference data for the second sensor at the second measuring site is used directly thereafter in step 108.

What is claimed is:

1. Method for operating a measuring site (1), wherein at least one measured variable is determined at the measuring site (1) by at least one first sensor (5) that can be calibrated, comprising the steps of:
    calibrating the first sensor (5) at presettable calibration points in time, storing at least one parameter in conjunction with calibration as a part of reference data of the first sensor (5) and estimating at least one aging-dependent variable of a second sensor (8, 6) based on the reference data of the first sensor (5), and calibrating or replacing the second sensor when results of the estimation indicate such should be performed, wherein the second sensor (5) is replaced by a replacement sensor (8) based on the results of the estimation, wherein the replacement sensor (8) is calibrated at the presettable calibration points in time and wherein at least one parameter in conjunction with calibration is combined with the reference data of the first sensor (5) into sensor-type reference data of the measuring site (1) and performing measurements based on the determined calibration data at a second measuring site.

2. Method according to claim 1, wherein the first sensor (5) is calibrated until at least one of the first sensor (5) malfunctions and data in conjunction with calibration lie outside of a given tolerance band.

3. Method according to claim 1, wherein a point in time is estimated as the aging-dependent variable.

4. Method according to claim 3, wherein only one such point in time is estimated for the second sensor (8, 6), the point in time lying temporally within a period of time spanning the points of time of calibration of the first sensor (5).

5. Method according to claim 1, wherein the second sensor (5) is replaced by a replacement sensor (8) based the results of the estimation.

6. Method according to claim 1, wherein at least one measured variable is determined at a second measuring site (2) by at least one second sensor (6) and wherein at least one aging-dependent variable of the second sensor (6) is estimated based on the reference data of the first sensor (5) which is at a first measuring site that is different from the second measuring site.

7. Method according to claim 1, wherein at least one of the pH value, the oxygen content, the chlorine content, the conductivity, the ozone content, the hydrogen peroxide content, the content of free chlorine, the content of residual chlorine, the turbidity, and the solids content is determined as said at least one measured variable with the first sensor (5).

* * * * *